(12) United States Patent
Moreland et al.

(10) Patent No.: US 10,179,186 B2
(45) Date of Patent: Jan. 15, 2019

(54) WOUND CARE ARTICLES

(71) Applicant: Ansell Limited, Richmond, Victoria (AU)

(72) Inventors: Jeffrey Moreland, Simpsonville, SC (US); Roger Eugene Huckfeldt, Nixa, MO (US); Dion Ross, Union, NJ (US); Eric Thompson, Central, SC (US); Jamie Ashworth, Freehold, NJ (US); Michael Zedalis, Mendham, NJ (US); Anthony B. Lopez, Somerset, NJ (US)

(73) Assignee: Ansell Limited, Victoria (AU)

( * ) Notice: Subject to any disclaimer, the term of this patent is extended or adjusted under 35 U.S.C. 154(b) by 249 days.

(21) Appl. No.: 13/928,644

(22) Filed: Jun. 27, 2013

(65) Prior Publication Data

US 2014/0005616 A1    Jan. 2, 2014

Related U.S. Application Data

(60) Provisional application No. 61/666,479, filed on Jun. 29, 2012, provisional application No. 61/734,632, filed on Dec. 7, 2012.

(51) Int. Cl.
*A61M 35/00* (2006.01)
*A61F 13/00* (2006.01)
(Continued)

(52) U.S. Cl.
CPC ........ *A61L 15/44* (2013.01); *A61F 13/00063* (2013.01); *A61F 13/08* (2013.01); *A61F 13/104* (2013.01); *A61L 15/26* (2013.01); *A61L 15/28* (2013.01); *D04B 1/16* (2013.01); *D04B 1/28* (2013.01); *A41D 19/0068* (2013.01);
(Continued)

(58) Field of Classification Search
CPC .... D04B 1/28; D04B 1/14; D04B 1/16; A61F 13/00063; A61F 13/0223; A61F 13/08; A61F 13/104; A61F 2013/00119; A61F 2013/00238; A61F 2013/00906; A61F 2013/0091; A61L 15/44; A61L 15/26; A61L 15/28; A61L 2300/102; D10B 2403/0114; D10B 2501/041; D10B 2501/042; D10B 2501/043;
(Continued)

(56) References Cited

U.S. PATENT DOCUMENTS 5,328,449 A    7/1994  Andrews et al.
6,087,549 A    7/2000  Flick
(Continued)

FOREIGN PATENT DOCUMENTS

CN    2175523 Y  *  8/1994
CN    2175523 Y     8/1994
(Continued)

OTHER PUBLICATIONS

International Search Report and Written Opinion mailed Oct. 11, 2013 for Application No. PCT/US2013/048175.
(Continued)

*Primary Examiner* — Andrew J Mensh
(74) *Attorney, Agent, or Firm* — Moser Taboada

(57) ABSTRACT

Single layer and multi-layer anti-microbial wound care fabrics, gloves, sleeves, anklets, socks, finger cots, masks, and similar wound care articles are disclosed.

13 Claims, 12 Drawing Sheets

(51) Int. Cl.

| | | |
|---|---|---|
| *A61L 15/44* | (2006.01) | |
| *A61L 15/26* | (2006.01) | |
| *A61L 15/28* | (2006.01) | |
| *D04B 1/16* | (2006.01) | |
| *D04B 1/28* | (2006.01) | |
| *A61F 13/08* | (2006.01) | |
| *A61F 13/10* | (2006.01) | |
| *A61F 15/00* | (2006.01) | |
| *D04B 1/14* | (2006.01) | |
| *A41D 19/00* | (2006.01) | |
| *B29D 99/00* | (2010.01) | |

(52) U.S. Cl.
CPC .............. *A61F 2013/0091* (2013.01); *A61F 2013/00119* (2013.01); *A61F 2013/00238* (2013.01); *A61F 2013/00906* (2013.01); *A61L 2300/102* (2013.01); *B29D 99/0067* (2013.01); *D04B 1/14* (2013.01); *D10B 2403/0114* (2013.01); *D10B 2501/041* (2013.01); *D10B 2501/042* (2013.01); *D10B 2501/043* (2013.01); *D10B 2509/022* (2013.01); *Y10S 2/917* (2013.01); *Y10S 424/13* (2013.01)

(58) Field of Classification Search
CPC .......... D10B 2509/022; A41D 19/0068; B29D 99/0067; Y10S 2/917; Y10S 424/13
USPC .................. 604/292, 303, 304; 424/409, 402
See application file for complete search history.

(56) References Cited

U.S. PATENT DOCUMENTS

| | | | |
|---|---|---|---|
| 6,155,084 A | 12/2000 | Andrews et al. | |
| 6,194,332 B1 | 2/2001 | Rock et al. | |
| 6,861,570 B1 | 3/2005 | Flick | |
| 6,962,064 B1 | 11/2005 | Hardee et al. | |
| 7,005,556 B1 | 2/2006 | Becker et al. | |
| 7,213,419 B2 | 5/2007 | Hardee et al. | |
| 7,214,847 B1 | 5/2007 | Flick | |
| 7,230,153 B2 | 6/2007 | Flick | |
| 7,246,509 B2 | 7/2007 | Hardee et al. | |
| 7,310,824 B2 | 12/2007 | Walsh | |
| 7,434,422 B2 | 10/2008 | Thompson et al. | |
| 7,555,921 B2 | 7/2009 | Thompson et al. | |
| 7,678,718 B2 | 3/2010 | Harris et al. | |
| 7,713,252 B2 | 5/2010 | Greene et al. | |
| 7,814,570 B2 | 10/2010 | Hassan et al. | |
| 7,814,571 B2 | 10/2010 | Thompson et al. | |
| 8,110,717 B2 | 2/2012 | Gladman et al. | |
| 8,118,791 B2 | 2/2012 | Flick et al. | |
| 8,283,513 B2 | 10/2012 | Becker et al. | |
| 8,293,964 B2 | 10/2012 | Becker et al. | |
| 2006/0127462 A1 | 6/2006 | Canada et al. | |
| 2006/0143767 A1* | 7/2006 | Yang .................... A41D 19/015 2/16 |
| 2006/0264796 A1 | 11/2006 | Flick et al. | |
| 2007/0079636 A1 | 4/2007 | Mitchell | |
| 2007/0203442 A1 | 8/2007 | Bechert et al. | |
| 2007/0255193 A1* | 11/2007 | Patel ................ A61F 13/00029 602/48 |
| 2008/0064997 A1 | 3/2008 | Flick | |
| 2008/0233368 A1 | 9/2008 | Hartmann et al. | |
| 2008/0263747 A1* | 10/2008 | DeBlasis .................. A41F 1/06 2/161.1 |
| 2010/0030171 A1 | 2/2010 | Canada et al. | |
| 2010/0055437 A1 | 3/2010 | Fink et al. | |
| 2010/0234785 A1 | 9/2010 | Liebowitz | |
| 2010/0275342 A1 | 11/2010 | Sweeney et al. | |

FOREIGN PATENT DOCUMENTS

| | | |
|---|---|---|
| CN | 2175523 Y | 8/1994 |
| CN | 101080319 A | 11/2007 |
| CN | 102112078 A | 6/2011 |
| CN | 202000067 U | 10/2011 |
| JP | 61-048773 | 4/1986 |
| JP | 7-509157 | 10/1995 |
| JP | 2000-034640 | 2/2000 |
| JP | 2004-515267 | 5/2004 |
| JP | 2008-538705 | 11/2008 |
| WO | WO00/67600 | 5/2000 |
| WO | WO-2006088342 A1 | 8/2006 |
| WO | WO-2009071894 A1 | 6/2009 |

OTHER PUBLICATIONS

European Office Action dated Jan. 29, 2016 for European Application No. 13810437.7.
Chinese Office Action dated Jun. 2, 2016 for Application No. 201380024736.6.
Australian Patent Examination Report dated Oct. 19, 2016 for Patent Application No. 2013280222.
Chinese office action and search report dated Feb. 24, 2017 for Application No. 201380024736.6, 9 pgs.
European office action dated Jun. 8, 2017 for Application No. 13 810 437.7, 5 pgs.
Japanese notice of reasons for rejection dated May 23, 2017 for Application No. P2015-520501, 6 pgs.
Mexican agent correspondence dated Jun. 30, 2017 for Application No. MX/a/2015/000146, 2 pgs.

* cited by examiner

WOUND CARE ARTICLES

CROSS-REFERENCE TO RELATED APPLICATIONS

This application claims the benefit of U.S. Provisional Application No. 61/666,479, filed on Jun. 29, 2012 and U.S. Provisional Application No. 61/734,632, filed on Dec. 7, 2012, each of which is incorporated herein in its entirety.

BACKGROUND

Field of the Invention

Embodiments of the present invention generally relate to wound care articles and, more particularly, to wound care gloves, anklets, knee and elbow supports, masks, skullcaps, finger cots, and the like, comprising moisture-wicking and/or antimicrobial elements. Methods of fabricating the articles are also disclosed.

Description of the Related Art

Gloves, anklets, finger cots, knee and elbow supports, masks, skullcaps, and like articles are used to protect the hands, face, scalp, wrists, knees, and other joints of users. These articles have also found utility in the medical industry for wound care following cuts, abrasions, and chemical-, heat- and flame-caused burns. However, such injuries are often difficult to dress because joints move and, therefore, any dressing needs to accommodate this movement while remaining in intimate contact thereto. Furthermore, such articles can be used at all stages of care, for example, while in intensive care, emergency rooms, and outpatient and hospice care. Moreover, burn treatment often requires multiple changes of dressings.

Many such articles have synthetic or natural polymeric coatings to provide substantially impervious properties. Although impervious properties promote protection against germs, viruses, and the like, these articles also trap moisture and, in particular, trap perspiration inside the article. Moreover, during, for example, burn treatment, skin secretes moisture and exudates. Gloves and other wound care articles that trap moisture feel clammy and uncomfortable to the user and allow a septic, unhygienic environment to form in which microbes prosper. In addition, many wearable articles are rigid, stiff fabrics and have seams, imparting even additional stiffness, leading to stress and irritation during donning, usage, and doffing. Furthermore, skin sticks to dressings and other wearable articles, such as gloves, anklets, finger cots, and the like, during healing, which occurs particularly at joints, such as the knee, knuckles, ankles, elbow, and other areas where the article most tightly contacts a user's skin, which poses problems in removing dressings for viewing wounds or replacing the wound dressing as is often required.

Therefore, there is a need in the art for anti-microbial articles that manage moisture and perspiration, are flexible for a tight and comfortable fit during mobility, don and doff easily, can optionally be used with substantially cylindrical compression sleeves, and promote healing by allowing intimate contact of the article having the antimicrobial with the skin of the wearer without sticking to or abrading the skin/wound.

SUMMARY

Embodiments of the invention include an apparatus and methods for making wearable, easy to don and doff anti-microbial articles substantially as shown in and/or described in connection with at least one of the figures, as set forth more completely in the claims. Various advantages, aspects, and novel features of the present disclosure, as well as details of an exemplary embodiment thereof, will be more fully understood from the following description and drawings.

BRIEF DESCRIPTION OF THE DRAWINGS

So that the manner in which the above recited features of the present invention can be understood in detail, a more particular description of the invention, summarized above, may be had by reference to embodiments, some of which are illustrated in the appended drawings. It is to be noted that the appended drawings illustrate typical embodiments of this invention and are not to be considered limiting of its scope, for the invention admits to other equally effective embodiments. It is to be understood that elements and features of one embodiment may be in other embodiments without further recitation. Also, where possible, identical reference numerals have been used to indicate comparable elements common to the figures.

DETAILED DESCRIPTION

Figure 1:
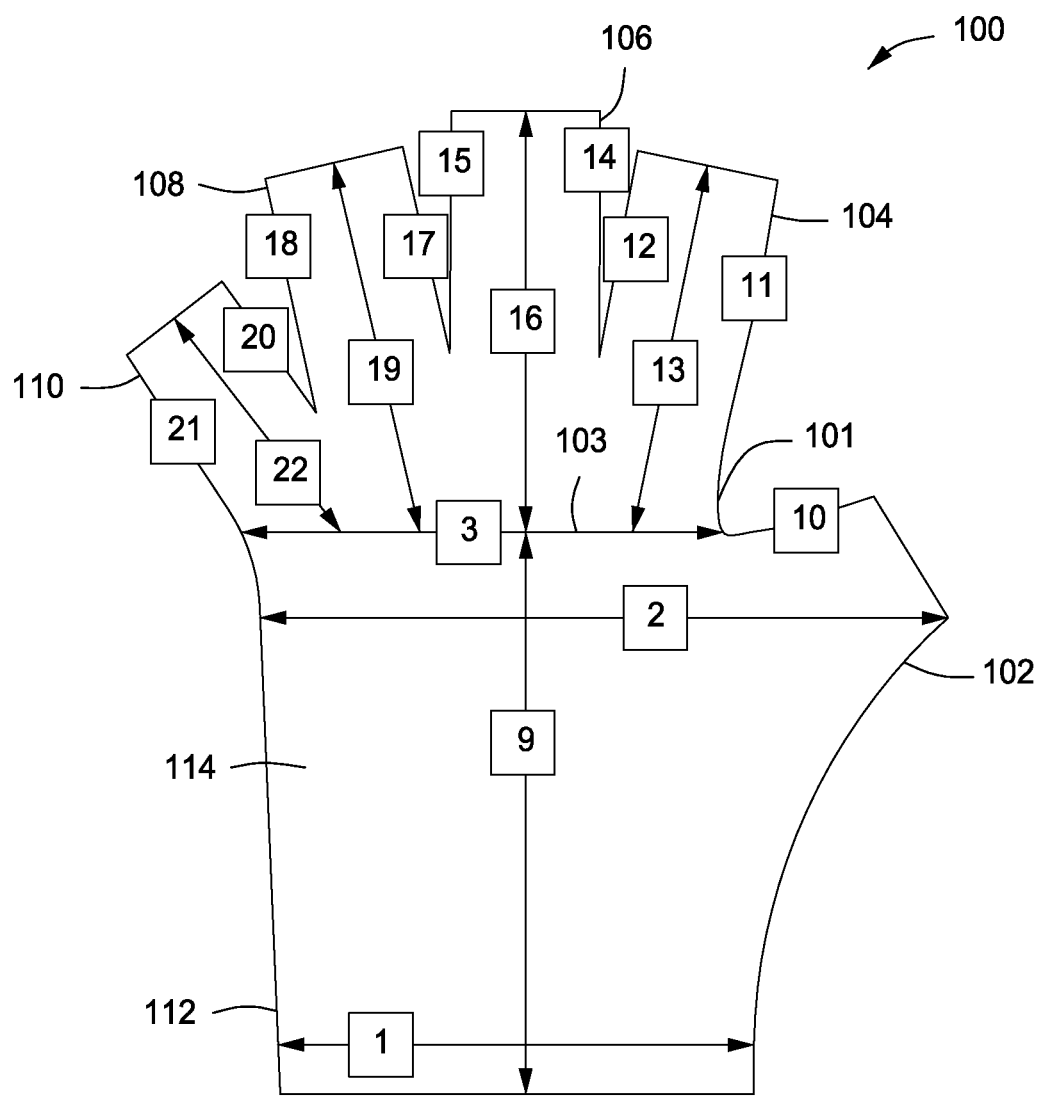
FIG. 1 depicts a glove according to embodiments of the invention.

Embodiments of the present invention comprise articles having a first yarn, to produce a layer that can be knitted with a second yarn having an antimicrobial agent to form the article, such as a glove, anklet, wristlet, sock, mask, finger cot, and other sleeves used to treat burns. The articles further comprise a layer having a moisture wicking fiber and/or an elastic yarn, and a layer comprising an antimicrobial agent for the treatment of wounds, wherein the inner layer does not stick to wounds and the second yarn promotes the wicking of moisture from one area, such as a wound, to a second layer and the transport of an antimicrobial agent to the wounds of a user. The article may be knitted by conventional knitting processes and may further comprise various deniers of yarns and gauges, which can be used to increase the channeling efficiency and distribution of moisture from one area of the article to other areas and to the outer layer.

Knitted articles may be seamless and comprise one or more yarns. In embodiments of the invention, a first layer is an absorbent, moisture-wicking knitted layer having an antimicrobial layer for the treatment of wounds and the second layer comprises cotton, polyesters, nylons, SPAN-DEX®, and the like and/or any combination of these yarns, imparting stretch and comfort properties. In some embodiments, the first layer is an inner layer, which contacts the skin of the wearer, comprises a hydrophilic yarn capable of transferring metals, such as silver, gold, or zinc, or their alloys or combinations of elemental metals and alloys (or other antimicrobials as discussed below), to a wound of a wearer, which promotes healing and an antiseptic environment. A second layer may be disposed on the skin-contacting layer. In some embodiments, the articles comprise a third, fourth, or fifth layer disposed on the second layer, each having either or both of, cotton, polyesters, nylons, SPAN-DEX®, hydrophilic, and anti-microbial yarns. Furthermore, embodiments of the invention comprise cut-and-sewn fabrics.

In some embodiments, the hydrophilic yarn used is a nylon yarn, such as nylon 6,6 or Nilit® AQUARIUS yarn having irregular cross-sections for exceptional wicking properties. Nylons promote the transport of moisture from the wound to the outer layer. In some embodiments of the invention, a nylon yarn is used as a main yarn, while in other embodiments, nylon yarn may be plaited into a main yarn. In other embodiments of the invention, two or more yarns are plaited throughout the article and, accordingly, the article has two layers throughout the entire article. The inner and outer yarns may optionally comprise the same nylon yarn, a different nylon, or a non-nylon yarn. Micro-denier and multi-filament yarns also promote superior wicking action. Both the inner layer yarn and the outer layer yarn may be chemically treated with elemental metals, such as gold, copper, iodine, silver, or zinc or their alloys, a noble metal-ion, TRIOSYN®, triclosan, 2-propanol, quaternary ammonium compounds, n-halamines or compounds and combinations thereof, for their antimicrobial properties. Silver-zinc and silver-copper zeolites are also suitable antimicrobials, as well as other anti-microbials known to those in the art.

Hydrophilic yarns allow the transfer of metal ions from the yarn to the wound or eluent, promoting healing of the wound. Other suitable antimicrobial agents include, but are not limited to, polymeric biguanides and quaternary ammonium compounds, such as chlorhexidine gluconate. The layers of the article may further comprise padding in one or more areas of the article. Seamless, knitted articles offer improved fit, comfort, antimicrobial functionality as well as lower costs. Seamless knitted articles in accordance with embodiments of the invention also offer articles that stick to skin less than articles having seams and, furthermore, provide less friction against the skin of the user. Non-stick yarns are also contemplated according to embodiments of the invention. For example, any of the yarns disclosed herein may be blended with low surface tension yarns, such as modified polytetrafluoroethylene yarns and polyethylenes.

FIG. 1 depicts a glove 100 according to embodiments of the invention. The glove 100 comprises a thumb 102, an index finger 104, a middle finger 106, a ring finger 108, a pinky finger 110, a cuff 112, and a palm 114, which is knitted or optionally cut and sewn. The glove 100 may be made several different sizes. Referring to the reference numerals of FIG. 1, the width 1 of cuff 112 ranges from approximately four-and-one-half inches to five-and-one-half inches. The maximum palm width area 2, the maximum width of the glove 100, before any polymeric coating is disposed thereon, as discussed below, may range from approximately six-and-one-quarter inches to eight-and-five-eighths inches. The palm width 3 across the glove 100 to a crotch 101 of the thumb 102 between the index finger 104 and thumb 102 may range from approximately four-and-one-third inches to five-and-five-eighths inches. The thumb width 4 may range from approximately one inch to one-and-one-half inches. The index finger width 5 may range from approximately one inch to one-and-one-half inches. The middle finger width 6 may range from approximately one inch to one-and-one-half inches. The ring finger width 7 may range from approximately one inch to one-and-one-half inches. The pinky finger width 8 may range from approximately seven-eighths of an inch to one-and-one-quarter inches. All ranges recited herein are exemplary and embodiments of the invention admit to other sizes and dimensions. For example, gloves and other articles can be designed in similar proportions to fit the limbs and torso of small children.

The thumb seam length 10 may range in size from approximately one-and-one-half inches to two-and-one-half inches. The index finger seam length 11 (between the index finger 104 and the thumb 102) ranges from approximately three-and-one-quarter inches to five-and-one-quarter inches. The index finger seam length 12 (between the index finger 104 and middle finger 106) may range from approximately two inches to three-and-one-quarter inches. The index finger length 13 (as measured from the tip of the finger 104 to reference line 103) ranges from approximately three-and-three-eighths inches to five-and-one-quarter inches. The middle finger seam length 14 and 15 may range from approximately two-and-three-eighths inches to three-and-five-eighths inches. The middle finger length 16 may range from approximately four inches to five-and-three-quarter inches. The ring finger seam length 17 (between the ring finger 108 and middle finger 106) ranges from approximately two inches to three-and-three-eighths inches. The ring finger seam length 18 (between the ring finger 108 and pinky finger 110) ranges from approximately two-and-one-quarter inches to three-and-five-eighths inches. The ring finger length 19 may range from approximately three-and-three-eighths inches to five-and-one-quarter inches. The pinky finger seam length 20 (between the ring finger 108 and pinky finger 110) may range from approximately one-and-one-half inches to two-and-seven-eighths inches. The pinky finger seam length 21 ranges from approximately two inches to three-and-seven-eighths inches. The pinky finger length 22 may range from approximately two-and-three-eighths inches to four-and-one-quarter inches.

The cuff width 1 may optionally comprise a width that is the same size, slightly smaller, or slightly larger than the width of the glove (as measured across the thumb area 2). Cuffs that do not significantly taper or neck down from the hand or foot to fit the size of the wrist or ankle (as is common for gloves and anklets and articles for other body parts) will be larger and allow ease of donning and doffing. Each of the fingers, 102, 104, 106, 108, and 110 can optionally be capless, wherein the caps of the fingers are either not knitted or are removed, so that the fingertips of the wearer are exposed. Embodiments of the invention may further comprise wherein the articles are knitted in accordance with the Knitted Variable Stitch Design (KVSD) and/or three-dimensional, Automatic-Knit-Liner technologies as is disclosed in commonly-assigned U.S. Pat. Nos. 6,962,064; 7,213,419; 7,246,509; 7,434,422; and 7,555,921, each of which is hereby incorporated by reference in its entirety.

Articles in accordance with embodiments of the invention can be knit with a knitting machine according to instructions provided via computer programming. Double-layered zones for knitted articles may be formed using a variable plaiting process, increasing the stretch in key flex areas of the gloves by altering the number of plaited courses in each section, such as the knuckles or the crotch between the index finger and thumb. For example, stretchable multi-layer functional zones are formed by plaiting a second yarn, such as SPANDEX® or LYCRA®, every fourth course in areas of low flex of the outer layer. Furthermore, the flex in some areas may be increased by adding a different yarn every eighth course in sections where no second yarn was present. The use of every 4th and 8th course in the plaiting structure is for illustrative purposes only. The plaiting structure can range from every other course to every 9th course using machines, such as, but not limited to, models SFG-I, NSFG, and SWG, manufactured by Shima Seiki Mfg., Ltd.

The properties of knitted articles in embodiments of the invention can be varied without the addition of different yarns. For example, varying the stitch dimensions, such as yarn tension and needle depth, can produce articles having different levels of stretchability. The tension of the yarn may be varied by adjusting the tension of the yarn between a pinch roller and a knitting head by computer control of a knitting machine, as is disclosed in commonly-assigned U.S. Pat. No. 7,434,422. A layer that is knitted tighter will have less stretchability. Varying the depth of penetration of the knitting needle into the article, and by casting off or picking up additional stitches in a knitted course, can also affect stretchability. A shallower needle penetration produces an article that is tighter and more difficult to stretch.

Figure 2:
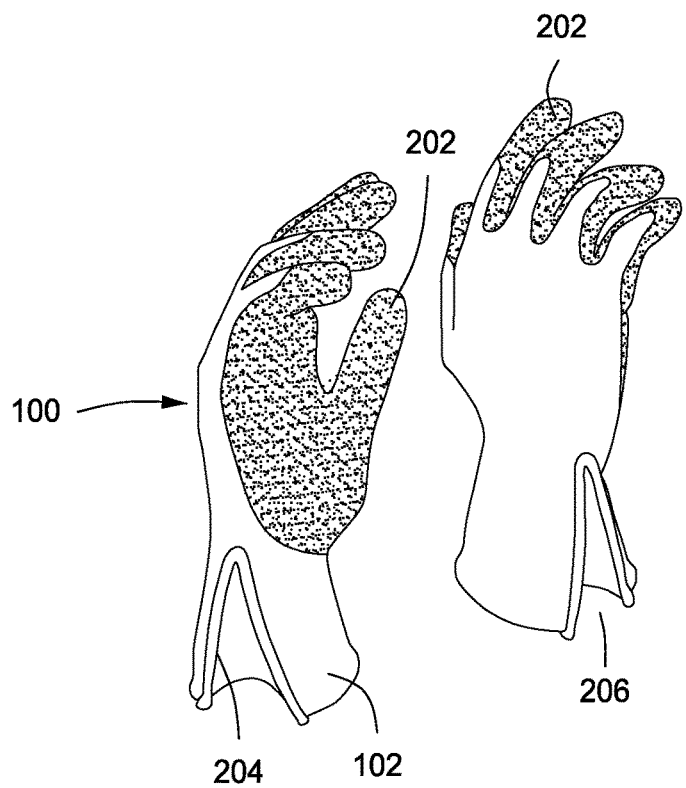
FIG. 2 depicts a glove having a slit cuff and coating disposed thereon, according to at least one embodiment of the invention.

FIG. 2 depicts the glove 100 having a slit cuff and coating disposed thereon, according to embodiments of the invention. In some embodiments, glove 100 includes a slit cuff 206 located on the pinky side of the glove 100, although other areas may have a slit, such as the thumb side. The glove 100, whether knitted or cut-and-sewn, may have one or more slits 206 along a longitudinal (as shown) or latitudinal axis, and along all or part of the article allowing the article to open and close in a clamshell-like manner for ease of donning and doffing over burned or wounded limbs, feet, hands, and the like. The slit 206 may traverse part of the article or the entire article. Articles in accordance with this principle may be opened and closed using non-permanent attachments, such as a strap and clasp (not shown), hook and loop fasteners 204, such as VELCRO®, and the like. In this context, the term non-permanent indicates the feature of being able to open and close the article multiple times without loss of attach-ability. As shown, the slit 206 traverses the side of the glove 100 on the cuff 102, exposing the side of the wearer's wrist. As will be discussed below, other embodiments comprise slits in different areas of a glove.

The glove 100, as shown in FIG. 2, may optionally comprise a polymeric coating 202. The polymeric coating 202 may be comprised of a natural latex, such as guayule or polyisoprene, a synthetic latex, such as carboxylated acrylonitrile butadiene, non-carboxylated acrylonitrile butadiene, butyl latex, polychloroprene, nitriles, polyurethane, and the like latex, polymeric, or elastomeric compositions, or blends thereof. The coating 202 may be formed on the glove 100 using the dip processes as described in commonly assigned U.S. Pat. No. 7,814,571, and U.S. patent application Ser. No. 12/769,829, each of which is incorporated herein by reference in its entirety. In FIG. 2, a palm dip is shown. The coating 202 optionally comprises a knuckle dip, finger dip, a three-quarters dip, and the like as needed for specific applications. Furthermore, before dipping in the polymeric coating, the gloves may be dipped in a coagulant, such as calcium nitrate or other coagulants known to those in the art, to destabilize the latex, promote gelling, and prevent strikethrough of the polymeric coating.

Figure 3:
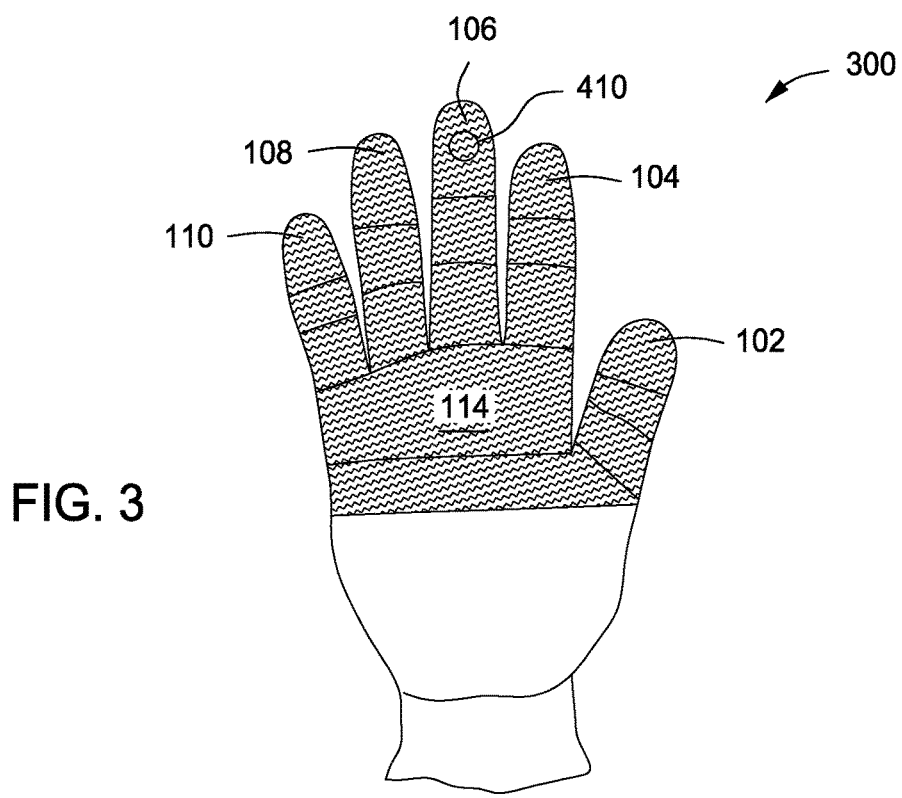
FIG. 3 depicts a glove according to embodiments of the invention.

FIG. 3 depicts a glove 300 according to at least one embodiment of the invention. In some embodiments, gloves and other articles in accordance with embodiments of the invention are knitted and subsequently inverted. FIG. 3 shows knitted courses on the thumb 102, index finger 104, middle finger 106, ring finger 108, pinky finger 110, and palm 114, which are shown as wavy lines, running perpendicular to the longitudinal length of the outside of the glove 300. The courses on the inside of the glove run parallel to the longitudinal length of the glove 300, resulting in the ease of donning and doffing because of lessened friction against the wearer's skin as discussed below. The combination of the use of stretchable yarns in the outer layer, such as SPANDEX® or LYCRA®, which may be knitted loosely as discussed above despite a snug fit with the afflicted body part, the disposition of the courses as described below, and the use of a clamshell like opening detachably adhered with fasteners, produces a glove allowing a snug fit with a minimal amount of irritation to the skin of the user or patient.

Figure 4:
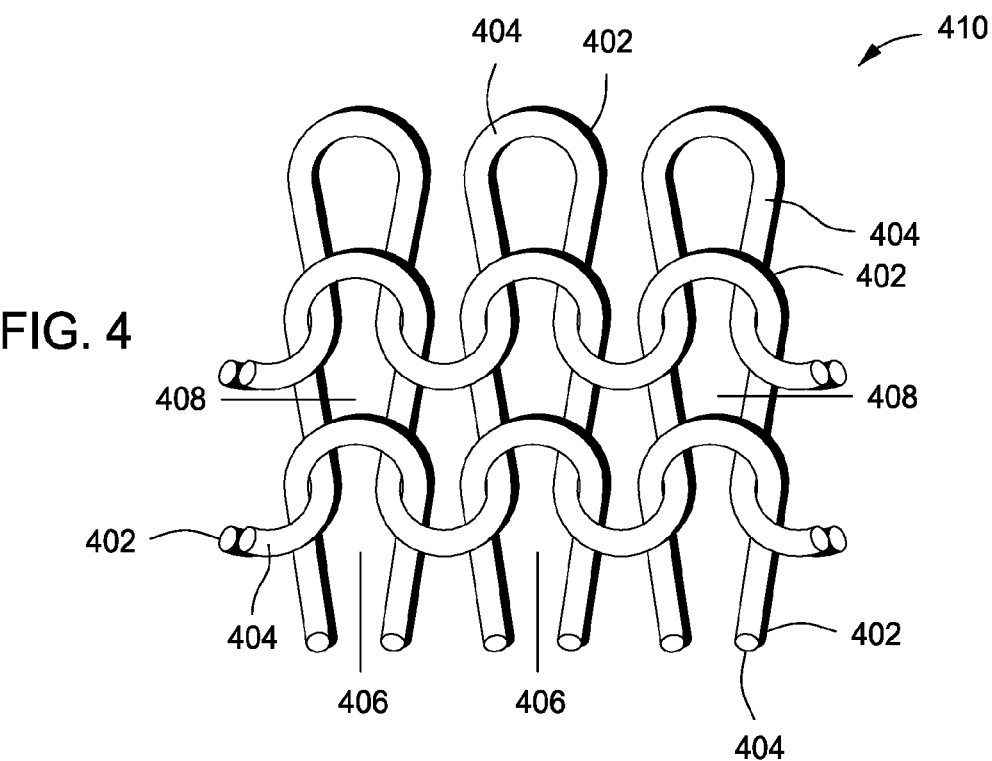
FIG. 4 depicts a close-up view of a knitted plaited fabric of a finger of FIG. 3, in accordance with embodiments of the invention.

FIG. 4 depicts a close-up view 410 of a knitted plaited fabric of the finger 106 of FIG. 3, in accordance with embodiments of the invention. The layer 402, which may be the inner layer, of the knitted plaited fabric of the finger 106 is shown in shading, which is the layer that contacts the skin of the wearer. As discussed above, the layer 402 comprises a hydrophilic yarn, such as a nylon, that is coated with an agent having antimicrobial activity, as discussed below. In some embodiments, the inner layer 402 comprises a nylon 6 or nylon 6,6 yarn that is coated with silver or another metal. The layer 404, which may be an outer layer, comprises cotton, polyesters, nylons, SPANDEX®, LYCRA®, and the like and/or any combination of these yarns. As shown, the layer 402 may be seamlessly plaited throughout the article. The courses of knitted fabrics create interstices between stitches of yarn. For example, the wicking channels 408 of the layer 404 run along an axis perpendicular to the longitudinal axis of the glove or, in other words, are horizontally as depicted. The wicking channels 406 of the layer 402, the side contacting the skin of a user, run along an axis parallel to the longitudinal axis of finger 106 of glove 300. When the wicking channels 406 are so situated, internal to a glove, the friction is lessened against the skin of a wearer of an article, maximizing the amount of stretching possible to accommodate swelling near a wound. Furthermore, yarns having irregular or non-circular cross sections can enhance a wicking action of liquids through spaces between yarns.

The inner plaited yarns will typically be lighter than the outer yarn, ranging in size from 70-1000 denier and needle gauges ranging from 10-18. Plaiting the inner antimicrobial layer in only certain areas, for example, the palm, the backhand, or the fingers, is also contemplated and reduces the overall cost of the glove because of the expense of the antimicrobial. The inner layer 402 may comprise a hydrophilic yarn, such as nylon 6,6, which contacts the skin of the wearer, promoting the wicking of moisture away from the skin, and is treated, such as by coating or other processes, with an antimicrobial agent, such as silver, to promote the transport of silver or silver ions from the yarn of the glove to the wound.

Figure 5:
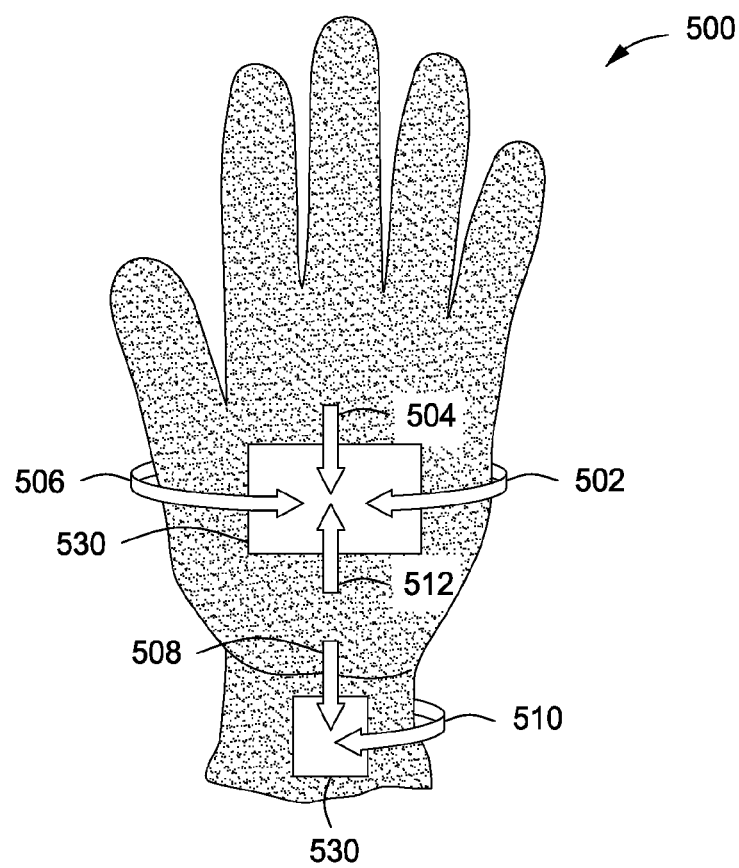
FIG. 5 depicts a glove having a highly-wicking yarn and moisture reservoir according to embodiments of the invention.

FIG. 5 depicts a glove having a highly-wicking yarn and moisture reservoir, according to embodiments of the invention. Layer 500 comprises a yarn that is made from a highly-wicking fiber, such as a nylon 6,6, marketed under the name Nilit® AQUARIUS by Nilit, Inc. of Martinsville, Va., the highly-wicking features of which are disclosed below. Other appropriate highly-wicking yarns include STA-COOL® polyester, ringspun hydrophilic polyester HYDROTEC®, or DRYENERGY® polyester/cotton and may further comprise any shape for the treatment of a limb or body part, such as a leg, arm, knee, ankle, head, waist, and the like. Micro-denier, multi-filament yarns, and yarns having non-circular, irregular cross-sections are particularly effective at wicking moisture away from one area, such as a wound, to other areas.

The layer 500 optionally comprises an absorbent material element 530, which is a water-scavenging absorbent reservoir. The absorbent material element 530, a super absorbent material, may be attached to a surface of the layer 500, desirably on or near back hand area and/or cuff area of the layer 500. The absorbent material element 530 can be attached to the layer 500 by stitching, a thermoplastic adhesive, glue, other suitable attachments, and the like. The yarn of the layer 500 is fluidly coupled to the absorbent material element 530 to facilitate wicking of perspiration or other fluids from one or more locations, such as indicated by directional arrows 502, 504, 506, 508, 510, and 512 of the glove to at least one absorbent material element 530. After the absorbent material element 530 is adhered to the layer 500, layer 500 may be placed on a former of a desired shape and coated with a polymeric coating as discussed above. Embodiments of the invention further comprise wherein the absorbent material element 530 is disposed or adhered on the palm or near or along the fingers or finger crotches.

The perspiration and moisture wicking properties may also be achieved as disclosed in commonly assigned U.S. Provisional Appl. Ser. No. 61/571,569, and U.S. patent application Ser. No. 13/538,368, which are incorporated herein by reference in entirety. This technology includes a super absorbent material comprised of an electrospun polyurethane and bound acrylate. One such super absorbent material is marketed as SNS Nanosorb® 28. SNS Nanosorb® 28 has a higher affinity for water compared with the nylon 6,6 of the inner knitted layer. The super absorbent material pulls in moisture wicked to it by the nylon yarn, which the super absorbent material subsequently pulls into its internal matrix. Such moisture movement leaves the nylon of the inner knitted layer dry, keeping the moisture away from a user's skin. Different thicknesses of the super absorbent material may be employed. Moreover, the super absorbent material can be used, in lieu of additional padding, to protect body parts from inadvertent bangs and bumps. Moisture absorption is also enhanced, in some embodiments of the invention, by the inclusion of poly-acrylates, polyurethanes, polyvinyl alcohol, hydrogels, and other hydrophilic materials.

Other embodiments of the invention may position reservoirs in various locations and have various shapes and thicknesses to promote comfort and/or absorbency. The backhand area and cuff area are good choices for locations for the reservoir because these areas see little strain and do not contact the skin of the user as tightly. In other words, moisture is removed from the palm and finger areas, which have relatively high concentrations of perspiration and are high strain areas, where the glove most tightly contacts the skin of the user during use, and is channeled to areas where there is little contact with skin.

The highly-wicking yarn of the layer 500 is capable of directing the moisture toward the cuff and back hand area having the absorbent material element, which draws moisture inward and therefore acts as a reservoir. By channeling the moisture away from the palm and fingers and to the center of the absorbent material element, a wet or clammy feeling is avoided, promoting hygiene and comfort. Moreover, the efficient and high transfer of the antimicrobial agent to the wounded skin of a patient promotes healing of the skin. In some embodiments of the invention, the absorbent material element 530 is on the cuff, which is not covered by the polymeric coating 202, allowing moisture to be evaporated from the absorbent material. Moisture may also be directed to other areas, such as to a wound instead of away from the wound. For example, skin conditions and creams, as well as other medicaments and medicines.

Figure 6:
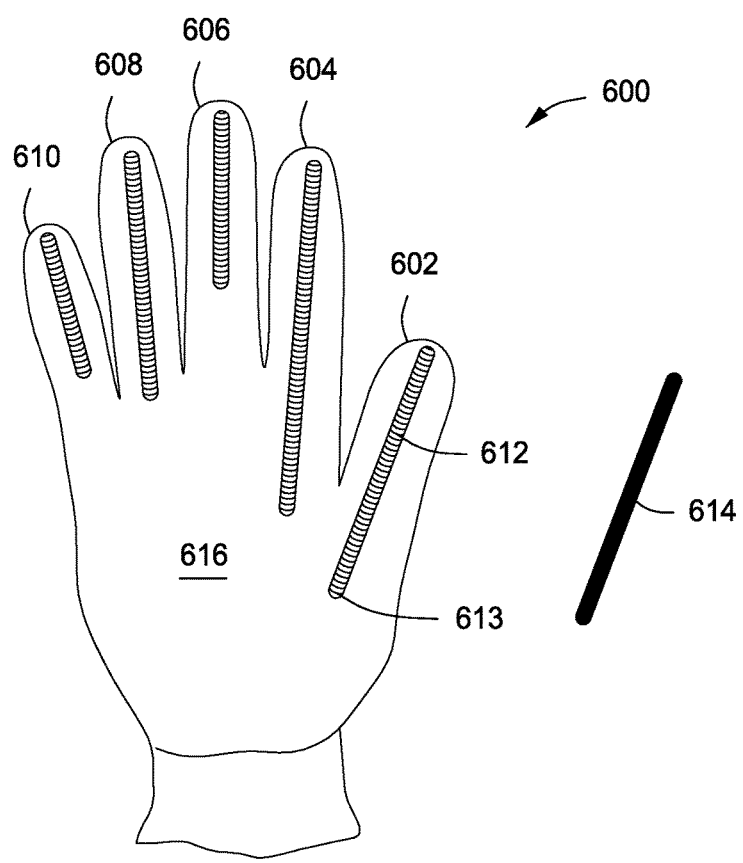
FIG. 6 depicts a left-hand glove, having conduits for accommodating resilient members, according to embodiments of the invention.

FIG. 6 depicts a left-hand glove 600, having conduits for accommodating resilient members, according to embodiments of the invention. The glove 600, which shows the back hand of the glove, includes a thumb 602 and fingers 604, 606, 608, and 610. Any or all of the thumb 602 and fingers 604, 606, 608, and 610 further comprise a conduit 612, which is capable of receiving a resilient member 614 for immobilizing one or more fingers or providing resistance for strengthening exercises. In some embodiments, the resilient member 614 comprises a compliant material and profile to promote hand strengthening. For example, a compliant plastic having a thin, flat profile, while providing resistance to flexing, nonetheless allows a wearer to flex all fingers. Accordingly, the strength of a weakened hand, for instance, after an accident, can be improved. As the hand of the wearer becomes stronger, the resilient member 614 can be changed to a stiffer material to provide additional resistance, allowing even greater strengthening to occur.

For some situations, such as an acute injury, for example, a burn or broken finger, it may behoove the wearer to have one or more knuckles or fingers immobilized. Therefore, in some embodiments, the resilient member 614 is made of, for example, steel, preventing the wearer from bending the fingers. In some embodiments, the conduit 612 is knitted into glove 600. The conduit 612 may traverse all of a finger or only part, for example, only one or two knuckles, such as is depicted in the finger 606. Alternatively, the length of the conduit 612 may extend into the backhand area 616, such as is depicted on the thumb 602 and finger 604. Also, the glove

600 may comprise truncated fingers, for example, open-ended fingers and thumbs, as is discussed below, so that the fingers of the wearer are uncovered. Furthermore, the conduit 612 is capable of receiving resilient member 614, for example, through a conduit opening 613. The conduit 612 may also be open for receiving resilient member on the distal end (not shown) of the thumb 602 or fingers 604, 606, 608, 610.

The resilient member 614 may be of variable thicknesses, widths, lengths, and profiles, for example, circular, square, rectangular, flat, and the like. Also, the resilient member 614 may comprise many different materials, for example, compliant plastics, such as polyethylene, or polypropylene, stiffer plastics, such as acrylonitrile-butadiene-styrene (ABS) or nylons, or very stiff, and/or impact-resistant plastics, such as polycarbonate or polyetherimide, and the like. Rubber materials, such as thermoplastic elastomers (TPE) and vulcanizates (TPV), can also be used where flexibility is desirable. In some embodiments, the resilient member 614 made of TPE or TPV, may be sewn into glove 600. The resilient member 614 also comprises metals, such as aluminum, steel, titanium, silver, silver alloys, zinc, zinc alloys, and the like. In some embodiments of the invention, silver and/or zinc ions, released from the resilient member, migrate, via an eluent or perspiration, to the wound, promoting healing. In some embodiments of the invention, the conduits 612 can accommodate electrical wires, irrigation, lighting, and mechanical pulleys, to aid in healing, movement, and post treatment. For example, the conduits 612 may be knitted of a electrically conductive yarn. In some embodiments, the conduits 612 extend from the end of the fingertips to the cuff area, where electrical connectors and power can be added to deliver electricity to wounds, promoting healing.

Figure 7:
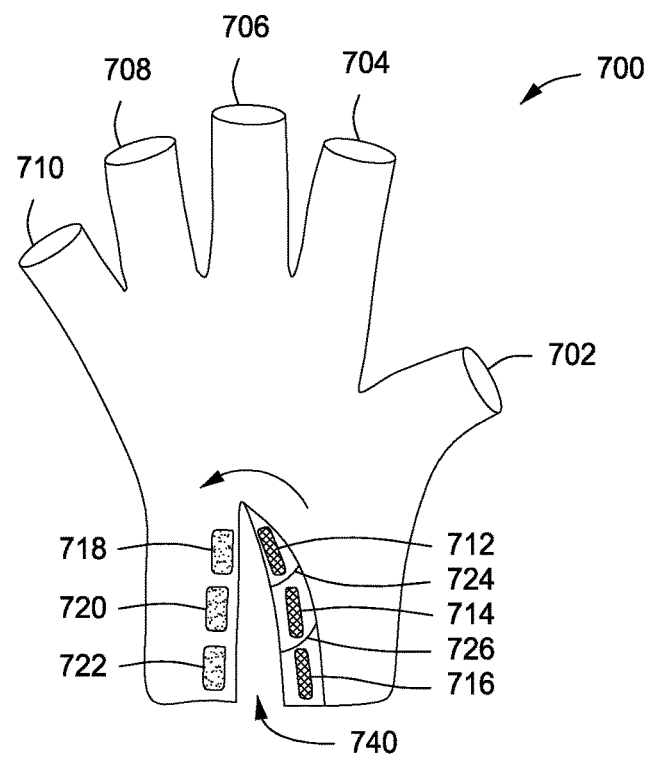
FIG. 7 depicts a perspective view of the palm side of right-handed glove, in accordance with embodiments of the invention.

FIG. 7 depicts a perspective view of the palm side of a right-handed glove 700, in accordance with embodiments of the invention. The glove 700 includes the thumb stall 702 and finger stalls 704, 706, 708, and 710. In some embodiments, the glove 700, as shown, has truncated thumb and finger stalls so that the fingertips of the wearer are not enclosed within the glove 700. Also included in the glove 700 are closure flaps 712, 714, and 716, which comprise hooks that mate with the corresponding members 718, 720, and 722 respectively to close a slit 740. In some embodiments, the hooks are VELCRO® hooks, and, in some embodiments, the hooks engage VELCRO® loops on the corresponding members 718, 720, and 722 to releasably close the slit 740. The slit 740, and VELCRO® closure flaps, can be on the palm or back of the hand, fingers, or thumb areas. VELCRO® closure flaps 712, 714, and 716 may adhere to the corresponding members as a single piece or, alternatively, be split in one or more places, such as at slots 724 and 726, so that not all closure flaps be opened to view the hand. In some embodiments, the finger stalls can be made to any length and cut shorter by an attending healthcare worker to better fit the patient. Moreover, in some embodiments, VELCRO® members 718, 720, and 722 are omitted and the hooks of VELCRO® closure flaps 712, 714, and 716 engage directly with the cut-and-sewn fabric or loops of a knitted article to releasably close the article. In some embodiments of the invention, the glove 700, comprising slit 740, may be cut-and-sewn or knitted so that the glove 700 can fit either a left-hand or a right-hand, i.e., be ambidextrous.

Figure 8:
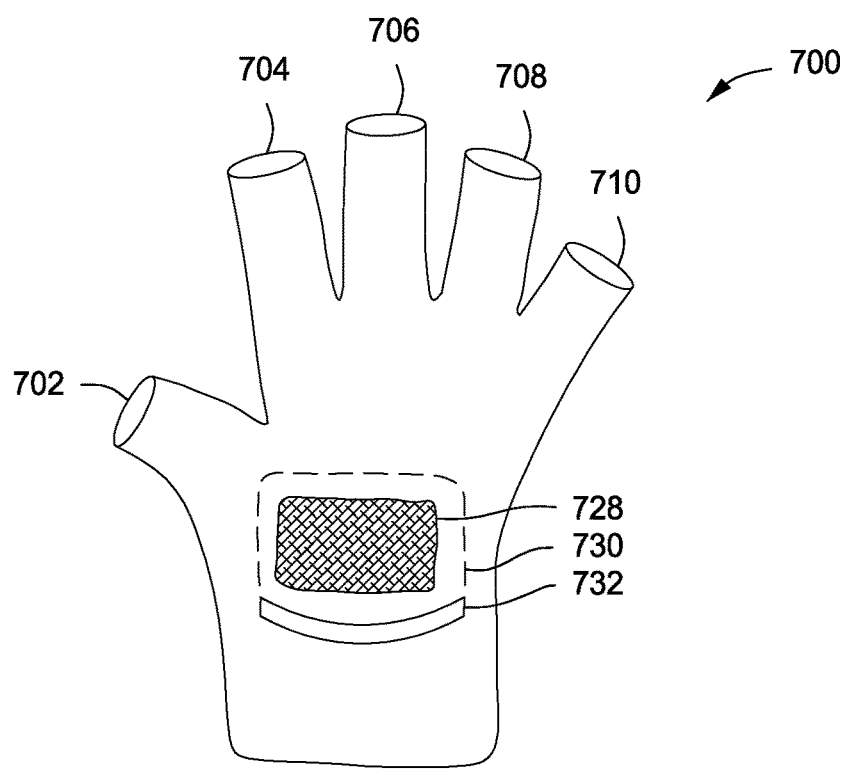
FIG. 8 depicts a perspective view of the backhand side of right-handed glove, in accordance with embodiments of the invention.

FIG. 8 depicts a perspective view of the backhand side of a right-handed glove 700, in accordance with embodiments of the invention. In FIG. 8, the glove 700 further comprises padding 728. The padding 728 may be a fabric, such as cotton, or a puncture- and/or impact-resistant material, such as a plastic, rubber, or metal. In some embodiments of the invention, the padding 728 is stitched or knitted directly onto the backhand of the glove 700, and may be plaited into the glove 700 or knitted into the glove seamlessly. In other embodiments, it may be adhered in other manners, such as by a padding that is cut and sewn onto the back hand area. In yet other embodiments, the glove 700 comprises a pocket 730 (shown partially by hidden lines). The pocket 730 includes an opening 732, which is capable of accommodating padding placed into it. In some embodiments, the glove 700 includes having padding 728 knitted directly within the glove 700 as well as having the pocket 730 knitted within the glove 700, allowing for double the amount of padding to be present. In some embodiments, the padding 728 could be soft for protection or hard to help hold a desired hand shape or curvature of the hand for therapy reasons.

Figure 9:
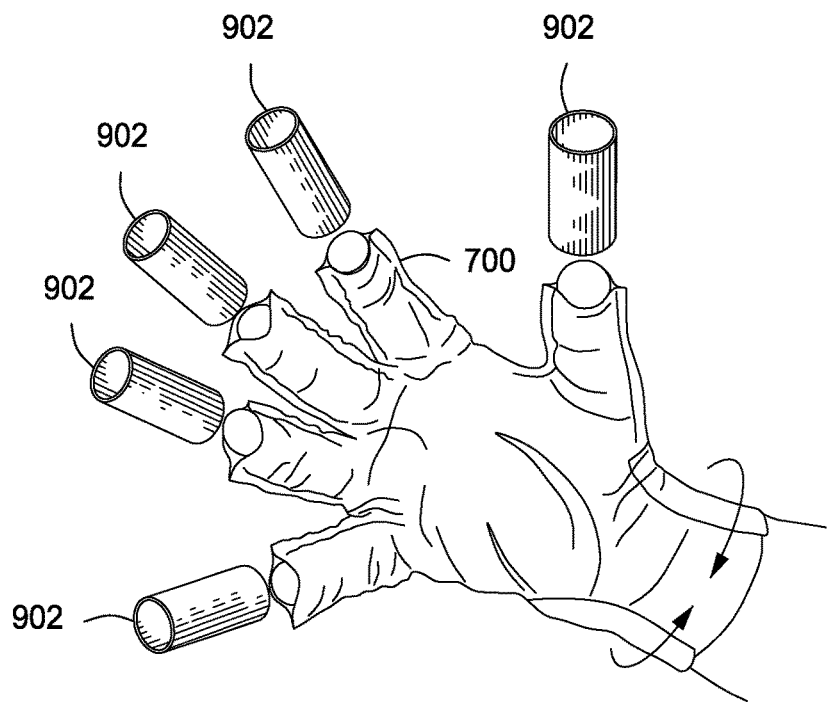
FIG. 9 depicts removable inserts and a cut-and-sewn glove in accordance with some embodiments of the invention.

FIG. 9 depicts removable inserts 902 and a cut-and-sewn glove in accordance with some embodiments of the invention. The removable insert 902 is a substantially conical or cylindrical member. The removable insert 902 may be made of any suitable smooth material, for example, plastics, metals, paper, or glass. The removable insert 902 may be of many sizes, and is approximately larger than the finger upon which it will be placed. The removable insert 902 is placed over the fingers and thumb of a patient to protect and minimize abrasion of the glove on the wound surface, which may be painful to the patient and further irritate already damaged skin. The glove 700 is then placed over the hand, after which the removable inserts 902 are removed. The removable insert 902 may also be used with finger cots, as discussed below. In particular, finger cots having two open ends and having closures, such as a drawstring and/or hook-and-loop closures, such as VELCRO®, or gloves or other wound care articles having closures allow the closure to be tightened at different tensions before the removable insert 902 is removed, allowing custom tightening.

Figure 10A:
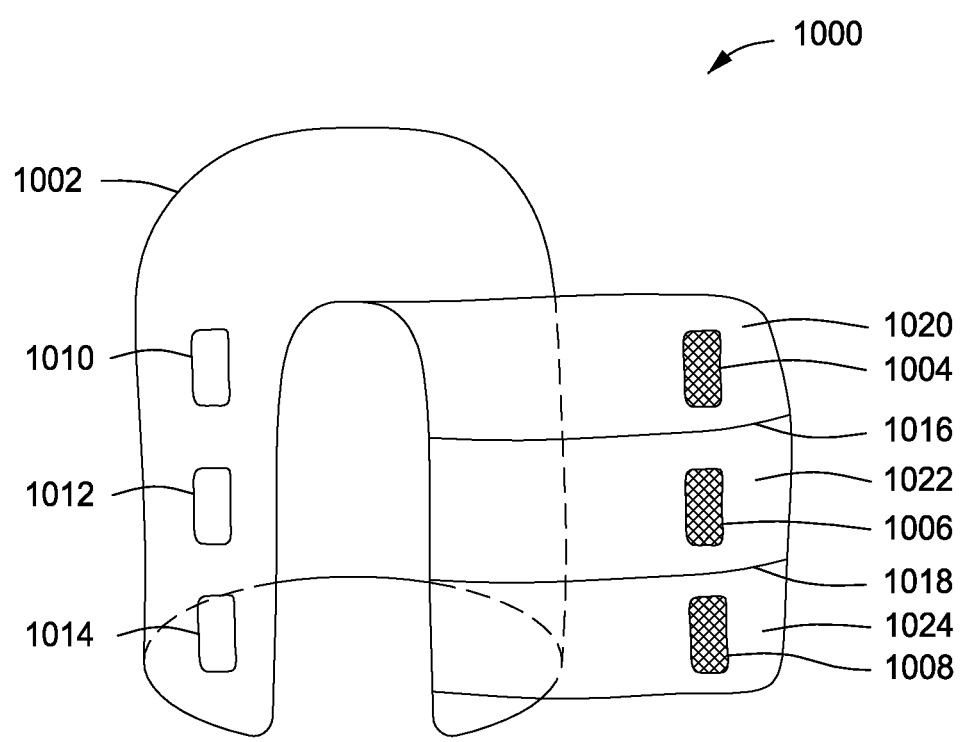
FIG. 10A depicts a finger cot having closures in accordance with some embodiments of the invention.

FIG. 10A depicts a finger cot 1000 in accordance with embodiments of the invention. The finger cot 1000, which can be knitted of a single or multiple yarns as discussed above, including a antimicrobial yarn, includes the finger covering 1002 and the closure flaps 1020, 1022, and 1024, which comprise hook and loop fasteners, such as VELCRO® strips 1004, 1006, and 1008, which mate with the corresponding VELCRO® members 1010, 1012, and 1014 respectively. VELCRO® closure flaps 1004, 1006, and 1008 may adhere to the corresponding members 1010, 1012, and 1014 as a single piece or, alternatively, be split in one or more places, such as at slots 1016 and 1018, so that each closure flap moves independently of the others. As discussed above, the hooks portion of the VELCRO® may be omitted, allowing the VELCRO® closure flaps 1004, 1006, and 1008 having hooks to engage and releasably close the closure flaps 1004, 1006, and 1008 directly.

The finger cot 1000 can be used on the tips of fingers and thumb with, for example, the glove 700, or without glove 700. The finger cot 1000 may be placed over the tip of a finger, for example, so that it is as long as one knuckle of the finger. Alternatively, the finger cot 1000 may be as long as the entire finger of the wearer, extending to the palm and backhand areas of the wearer's hand. The finger cots 1000 may be cut and sewn and comprising any suitable yarn. Alternatively, the finger cots 1000 may be knitted from any suitable yarn. In some embodiments, the finger cots 1000 are knitted using moisture control yarns as discussed above.

Moreover, the finger cots 1000 can be designed to treat burns, injuries, or other conditions sustained on toes.

Figure 10B:
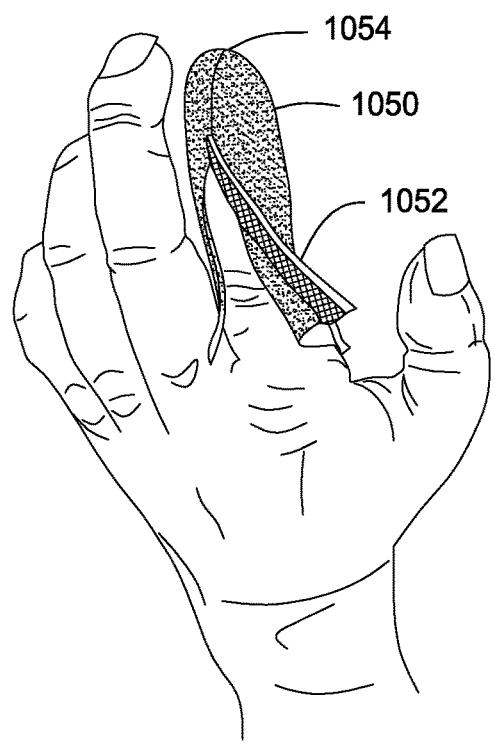
FIG. 10B depicts a finger cot having a longitudinal closure in accordance with some embodiments of the invention.

FIG. 10B depicts a finger cot 1050 having a longitudinal closure in accordance with some embodiments of the invention. The finger cot 1050 has a closed end at tip 1054. A closure 1052, which may be a VELCRO® closure, runs along the longitudinal axis of the finger cot 1050 on the back of the finger. The closure 1052 may optionally be placed on the palm side of the finger or either side of the finger (not shown).

Figure 10C:
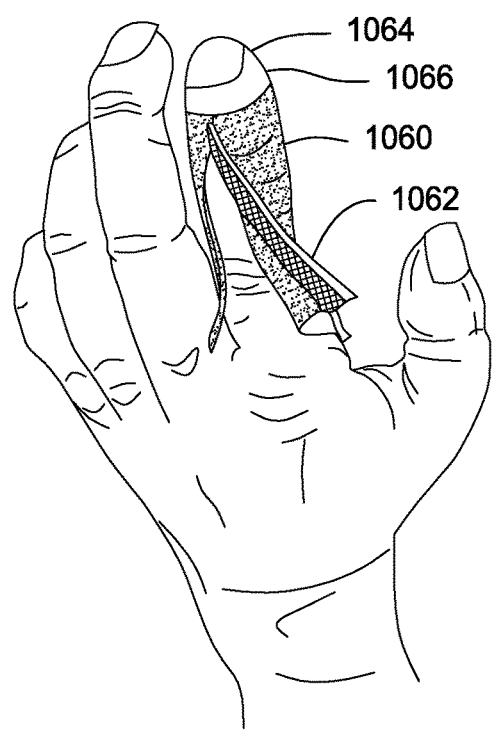
FIG. 10C depicts an open-ended finger cot having a longitudinal closure in accordance with some embodiments of the invention.

FIG. 10C depicts an open-ended finger cot 1060 having a longitudinal closure in accordance with some embodiments of the invention. The finger cot 1060 has an open end at a tip 1064, terminating at a ring 1066. A closure 1062, which may be a VELCRO® closure, runs along the longitudinal axis of the finger cot 1060 on the back of the finger. The closure 1062 may also optionally be placed on the palm side of the finger or either side of the finger. As discussed above, the finger cot 1060, because it is open ended, may be used with a removable insert, as discussed above, to prevent further injury to a wound when donning and doffing the finger cot 1060 or to custom tighten the closure 1062 of the finger cot 1060, allowing the removable insert to be removed after the closure is tightened.

Figure 11:
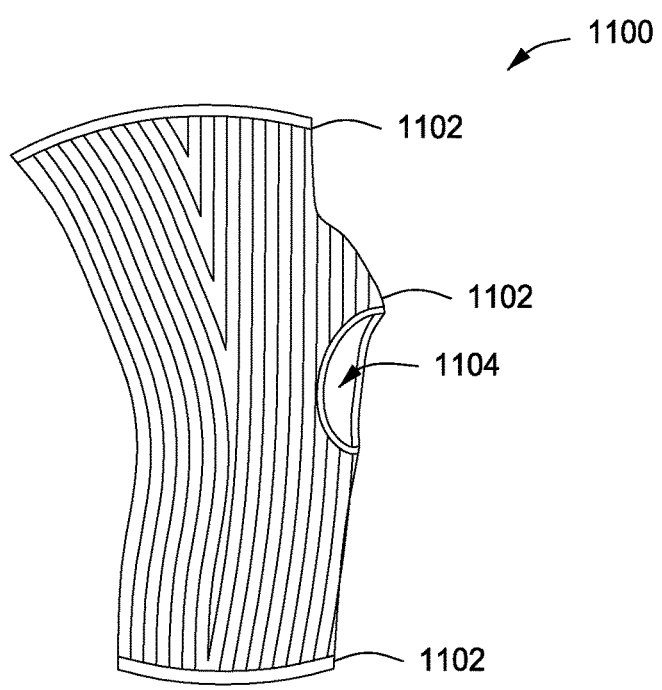
FIG. 11 depicts a side view of a wound care article for larger joints in accordance with embodiments of the invention.

FIG. 11 depicts a side view of a wound care article 1100 for larger joints in accordance with some embodiments of the invention. The wound care article 1100 can be used, for example, for a knee or elbow. The wound care article 1100 may be knitted or cut-and-sewn from a knitted, woven or non-woven fabric, in accordance with embodiments of the invention, and comprising yarns, super absorbent materials, VELCRO® closure flaps (not shown), and other features, such as releasably closable slits as discussed herein with respect to other embodiments of the invention. Moreover, the wound care article 1100 may be turned inside out so that the knitted courses run along the longitudinal axis of the article, so that during donning and doffing, less friction is imparted to the wearer as discussed above. The wound care article 1100 further comprises rings 1102, which maintain the article in place around the joint of the wearer, for example, an elbow, knee, shoulder, waist, hip, and the like. The wound care article 1100 further comprises a cut out 1104, allowing the tip of an elbow or knee cap to extend therethrough. The cut out 1104 therefore allows the limb of the wearer to be impacted less during bending or stretching.

Figure 12:
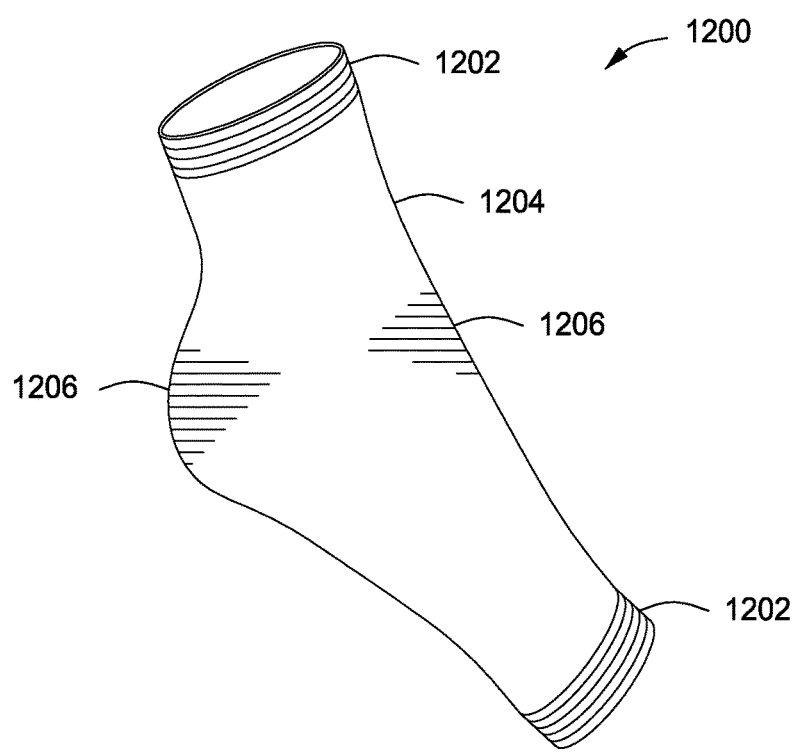
FIG. 12 depicts a perspective view of a wound care article in accordance with embodiments of the invention.

FIG. 12 depicts a perspective view of a wound care article 1200 in accordance with embodiments of the invention. The wound care article 1200 can be used, for example, for receiving an ankle or wrist. The wound care article 1200 is knitted or woven fabric, in accordance with embodiments of the invention. Moreover, wound care article 1200 may be turned inside out so that the knitted courses run along the longitudinal axis of the article, so that during donning and doffing, less friction is imparted to the wearer. The wound care article 1200 further comprises rings 1202, which may be knitted seamlessly using an elastic yarn, such as SPANDEX® or LYCRA® or a blend of a yarn having an elastic yarn, to maintain the article in place around the joint of the wearer, for example, an elbow, knee, shoulder, waist, hip, and the like.

The wound care article 1200 may further comprise a cut out (not shown) as discussed above, to allow, for example, a heel to extend therethrough. The wound care article 1200 may have a straight orientation while at rest, for example, having a straight edge 1204. Alternatively, the edge of the wound care article 1200 may be biased in a bent configuration (not shown). The wound care article 1200 further comprises elastic regions 1206, which provide a better fit to a body part and attenuate stretching of the wound care article in other areas, resulting in less movement and less friction. Less movement and friction in other areas, which might be impacted by burns or other injuries, allows for additional healing without being irritated or stressed by the movement.

Figure 13:
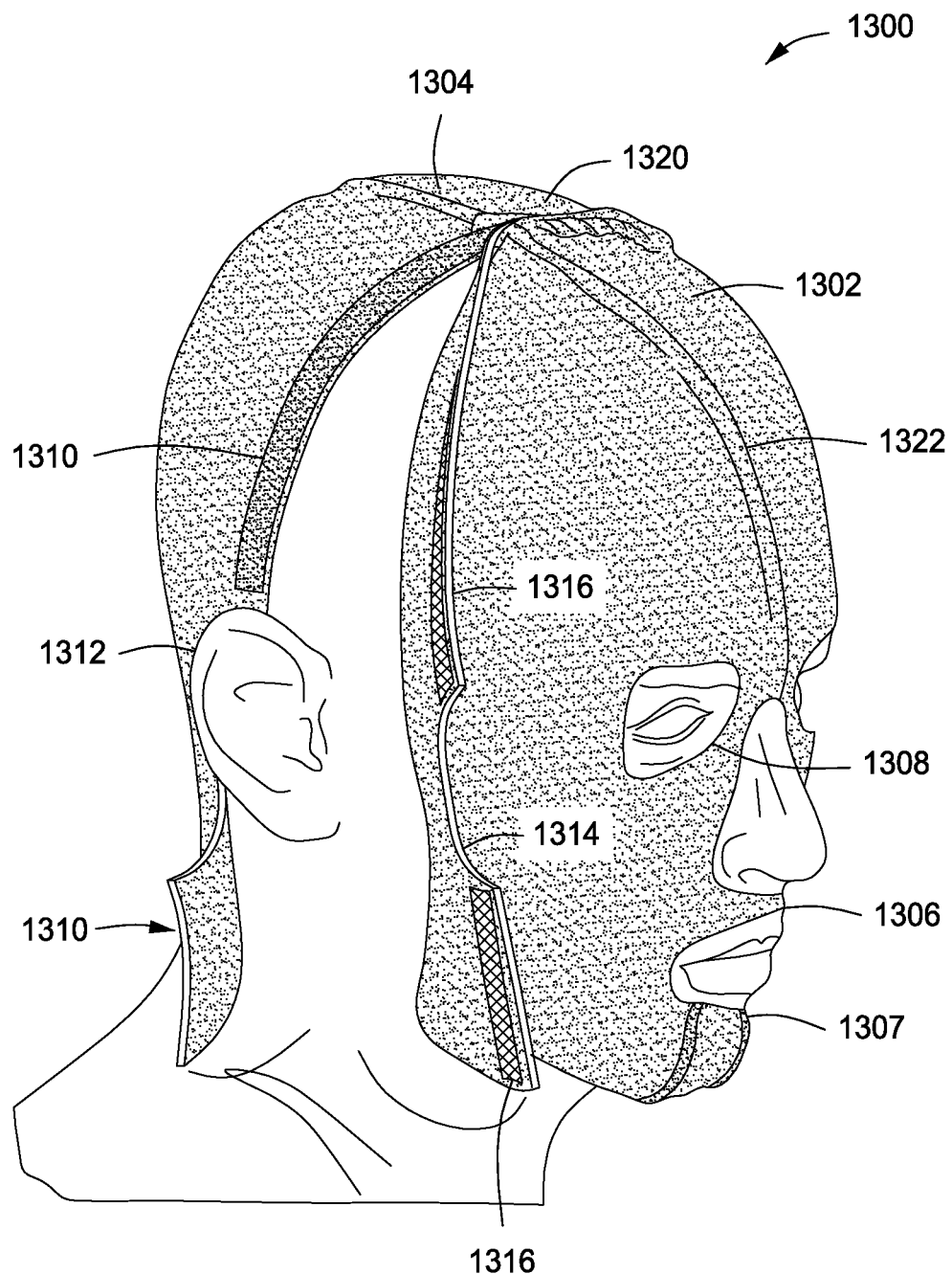
FIG. 13 depicts a wound care mask in accordance with embodiments of the invention.

FIG. 13 depicts a wound care mask 1300 in accordance with embodiments of the invention. The wound care mask 1300, as in other embodiments of the invention disclosed herein, comprises a knitted or woven outer layer that is an absorbent, moisture-wicking knitted layer and an inner layer that is an antimicrobial layer for the treatment of wounds. The outer layer may comprise cotton, polyesters, nylons, SPANDEX®, and the like and/or any combination of these yarns. The inner layer, which contacts the skin of the wearer, comprises a hydrophilic yarn capable of transferring metals, such as silver, gold, or zinc, or their alloys or combinations of elemental metals and alloys to a wound of a wearer, which promotes healing and an antiseptic environment. The inner layer also comprises moisture-wicking yarns capable of transferring water, moisture, and eluent away from the skin.

The wound care mask 1300 comprises a single part, two parts, or two or more parts releasably attached to one another. Irrespective of the number of parts comprising the wound care mask 1300, the wound care mask 1300 comprises closures or hook-and-loop fasteners 1310 and 1316, such as VELCRO®, which may overlapped to attach parts of the mask 1300. The closures or fasteners 1310 and 1316 may be disposed on wound care mask 1300 along an axis 1322 from the front of the mask 1302 to the back 1304, from the left side of the head to the right side of the head along axis 1320, or along both axes 1320 and 1322. The wound care mask 1300 comprises cutouts 1306, 1307, 1308, and 1312. For example, the cut out 1306 accommodates the nose of a wearer; the cut out 1307 accommodates the mouth of a wearer; the cut outs 1308 accommodate the eyes of a wearer; and the cut outs 1312 and 1314 accommodate the ears of a wearer. In embodiments of the invention, the mask has no cutouts. Attending healthcare personnel can take such a mask and make cutouts as needed for a specific person or injury. For example, if a nose, ear, or chin was burned badly, it would be a benefit to have that injury covered by the mask and without a secondary dressing. Moreover, this allows a one-size, fits-all mask. For example, the size and location of features varies from person to person. Eyes may be set further apart, the size of the nose and ears may different, etc., allowing healthcare personnel to make the cuts in the mask ensures a mask specific to the needs of the patient.

The width of the closures 1310 and 1316 can be varied to allow for a tighter or looser fit or to accommodate several sizes. For example, where the lateral width of the closures 1310 and 1316 are each approximately one inch wide, the size of the mark may be varied by nearly two inches per side. Also, because the wound care mask 1300 is made of yarn, it may be stretched tightly over the head of a wearer, creating compression. As discussed above, the loops of the VELCRO® or other fasteners can be omitted and the loops of the VELCRO® allowed to engage the fabric.

Outer dressings, which are placed over articles in accordance with embodiments of the invention, are further contemplated herein. Outer dressings are placed over the inner article, the skin-contacting article. The inner article can remain on the wound, for example a burn for an extended period of time, while the outer dressing might be changed every day. A burn patient can self-dress a wound easily and effectively once they were sent home from a hospital. As discussed below, this approach could be applied to gloves, finger cots, face masks and others articles.

Figure 14A:
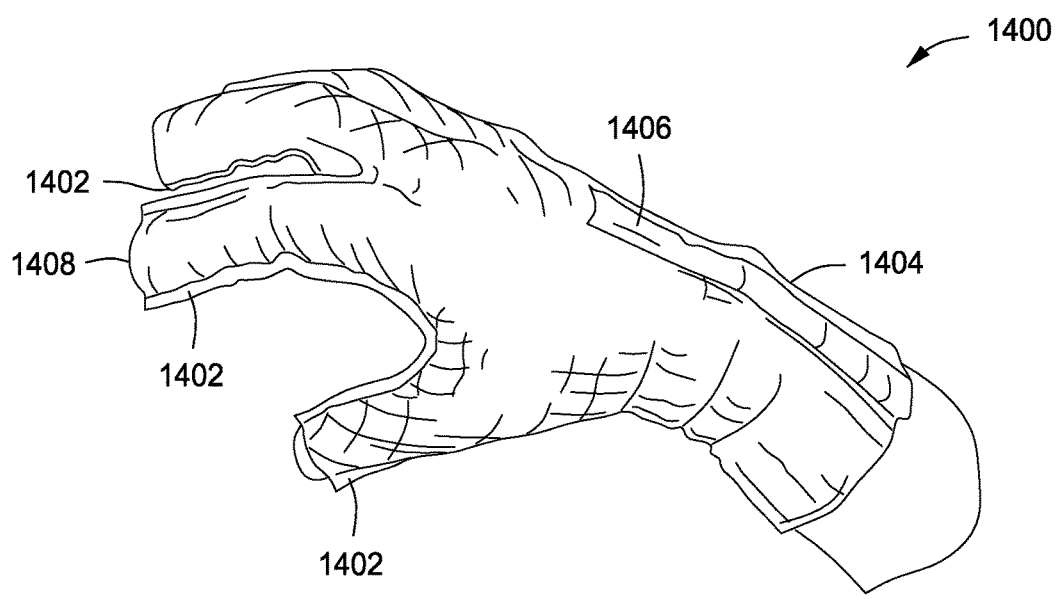
FIG. 14A depicts outer dressings in accordance with embodiments of the invention.

FIG. 14A depicts outer dressing 1400 in accordance with embodiments of the invention. The outer dressing 1400 is a dressing for use with a glove. It may be a knitted article or a woven fabric, substantially similar to articles disclosed herein, including the incorporation of silver, silver alloys, or other metals in yarns for anti-microbial effects. In some embodiments, the outer dressing 1400 is a 10-18 gauge knit. In some embodiments, it is a 13 gauge knit. Where a denser outer dressing is desirable, such as to absorb greater amounts of moisture, embodiments of the invention comprise an 18 gauge knit. In some embodiments, the yarn used to manufacture the skin-contacting article is a silver-coated nylon 6,6 yarn, such as the X-Static® yarn manufactured by Noble Biomaterials of Scranton, Pa. Alternatively, the skin-contacting article comprises a fabric containing an anti-microbial manufactured by Iftna, Inc. of Ontario, Canada. In some embodiments of the invention, the outerdressing 1400 is a bleached cotton overarticle, releasably placed over the skin-contacting article, and comprises an outer dressing for an anklet, sock, glove, mask, finger cot, sleeve, compression sleeve, elbow support, or knee support and the like.

The outer dressing 1400 comprises a yarn such as a rayon and/or cotton blend, where the cotton offers provides moisture absorption and the rayon is lubricious so that the outer dressing slides easily over the primary article. Yarns used to make the outer dressing 1400 could be a composite yarn used to make a single seamless layer. Alternatively, the outer dressing 1400 comprises a multi-layer having a main yarn and a plaited yarn. In such embodiments, the rayon layer may be on an inner layer and the cotton on an outer layer (not shown). The knit or woven fabric further comprises a highly elastic yarn, such as SPANDEX® or LYCRA®, so that, when the outer dressing is stretched during use, it clamps onto the primary article, i.e., skin-contacting article, in this embodiment, a glove, which holds the glove in place and tight to the skin.

The outer dressing 1400 may be a two-piece construction comprising a seam 1402. The seam 1402 further comprises VELCRO® fasteners as discussed herein. For embodiments of the invention in which outer dressing comprises two pieces, outer dressing 1400 can be placed over a glove and secured tightly or loosely with the VELCRO® fasteners at the seam 1402. The outer dressing 1400 further comprises fasteners along the backhand area 1406, such as VELCRO® fasteners 1404 (closed, as shown). In some embodiments, fasteners may alternatively or additionally be disposed along the palm area (not shown). This allows one to view the wound without having to remove the outer dressing 1400 entirely. Also, the outer dressing 1400 comprises truncated fingertips 1408 or, in some embodiments, where the fingertips are present (not shown).

Figure 14B:
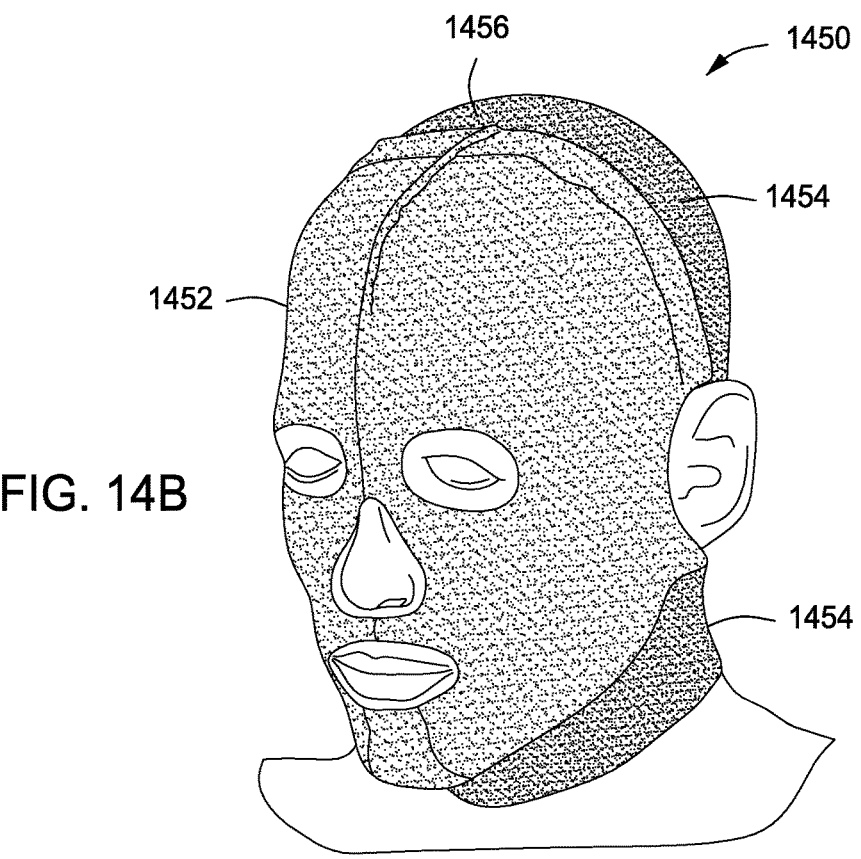
FIG. 14B depicts outer dressings in accordance with embodiments of the invention.

FIG. 14B depicts outer dressing 1450 in accordance with embodiments of the invention. The outer dressing 1450 is for use with a mask as discussed above. The outer dressing 1450 comprises all the benefits of the outer dressing 1400, including a two-piece construction, having two halves, which are adhered to each other releasably with fasteners, such as VELCRO®. As shown, the outer dressing 1450 has front half 1452 covering the inner mask 1454, which is a mask substantially as described above. The outer dressing 1450 may comprise the hooks of VELCRO® fasteners on one half, such as the front half 1452 while having the loops of the VELCRO® fasteners on the other half (not shown). Alternatively, as discussed above, the VELCRO® loops may be omitted. For example, where the front half 1452 has fasteners having hooks on an inside surface, the VELCRO® hooks may engage the yarn of the mask 1454 directly. Additional outer dressings may also be made in accordance with embodiments of the present invention, such as for articles disclosed herein for the fingers, knee, ankle, and the like.

Figure 15A:
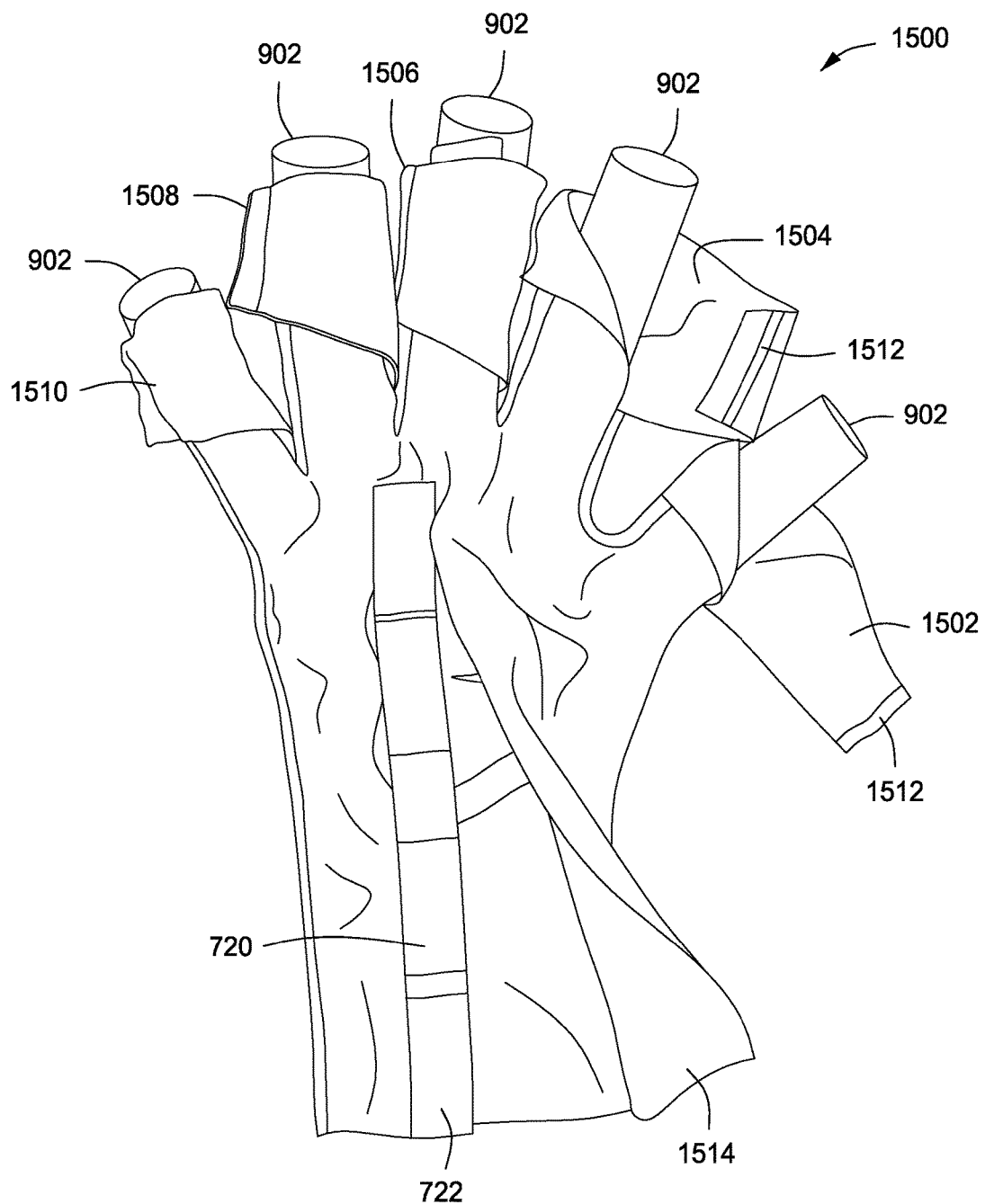
FIG. 15A depicts the palm side of right-handed glove, in accordance with embodiments of the invention.

FIG. 15A depicts the palm side of right-handed glove 1500, in accordance with embodiments of the invention. The glove 1500 includes a thumb flap 1502 and finger flaps 1504, 1506, 1508, 1510, and optionally a slit 1514. Any or all of thumb flap 1502, and finger flaps 1504, 1506, 1508, 1510, at their distal end 1512, comprise hook and loop fasteners. Although thumb flap 1502 and finger flaps 1504, 1506, 1508, 1510 may be wrapped around the fingers of a wearer, thus lessening the stress of donning and doffing, these can still be used in conjunction with removable insert 902, as discussed above.

In some embodiments, the glove 1500 comprises a knitted or woven structure, substantially similar to articles disclosed herein, including the incorporation of silver, silver alloys, or other metals in yarns for anti-microbial effects. In some embodiments of the invention, the glove 1500 is a woven and cut and sewn structure. The glove 1500 comprises two halves that are cut and sown together to form glove 1500, as discussed below. The glove 1500 further comprises hooks and loops, or optionally VELCRO® closures, on the palm or back of the hand to releasably close any slit within the glove. The hook and loops fasteners, or VELCRO® closures 720 and 722, may adhere to the corresponding members as a single piece or, alternatively, be split in one or more places so that not all closure flaps be opened to view the hand, as discussed above.

Figure 15B:
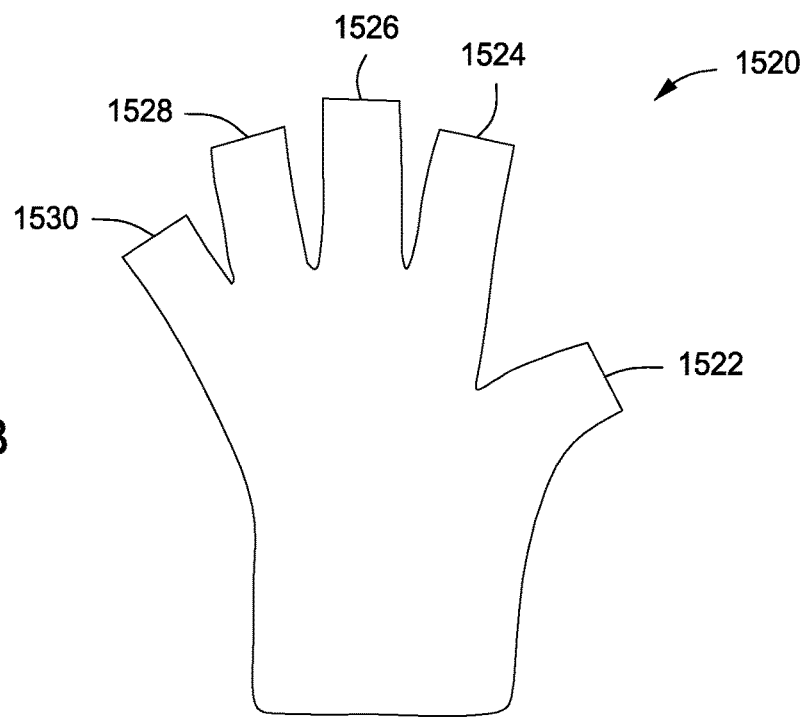
FIG. 15B depicts the backhand side of right-handed glove liner, in accordance with embodiments of the invention.

FIG. 15B depicts the backhand side of a right-handed glove liner 1520, in accordance with embodiments of the invention. For example, the glove half 1520 and may be sewn with another glove half 1520 to form the glove 1500. The glove half 1520 comprises thumb member 1522 and finger members 1524, 1526, 1528, and 1530.

Figure 15C:
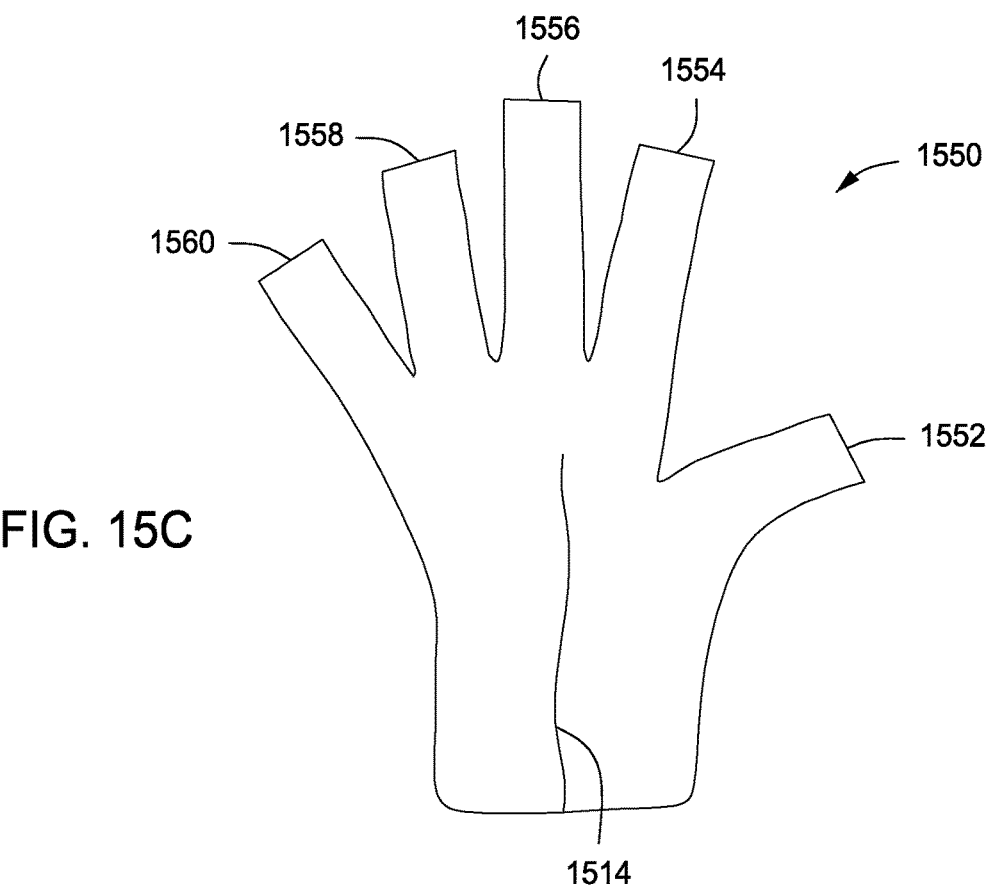
FIG. 15C depicts the palm side of right-handed liner, in accordance with embodiments of the invention.

FIG. 15C depicts the palm side of a right-handed liner 1550, in accordance with embodiments of the invention. Glove half 1550 comprises a thumb member 1552, and finger members 1554, 1556, 1558, and 1560 and optionally comprises a slit 1514. The thumb member 1552, and finger members 1554, 1556, 1558, and 1560 are longer than the corresponding thumb member 1522 finger members 1524, 1526, 1528, and 1530 of glove half 1520 as discussed above. The glove half 1550 can be sewn to glove half 1520 to create the glove 1500. The thumb members 1552, and finger members 1554, 1556, 1558, and 1560 are longer and may be wrapped around the fingers and thumb of the wearer without subjecting the wearer to the frictional forces of donning, which cause further painful abrasions and/or loss of skin tissue following a burn, as would be encountered with a conventional glove.

In some embodiments of the invention, the glove 1500 may be knitted comprising the thumb 1522 and finger members 1524, 1526, 1528, and 1530. Whether knitted or cut and sewn, glove 1500 further comprises the closures 1512 adhered thereto at a terminal end of thumb flaps and/or finger flaps. The closures 1512 may be, for example, hooks that engage loops on a corresponding area to hold the flap closed. The loops may be adhered to the flap or the loops may be the loops of a knitted article (not shown). In some embodiments, the hook and loops are VELCRO® closures. VELCRO® closures 1512 may also comprise hooks that engage the knitted or woven fabric to releasably close the thumb flap or finger flaps.

In some embodiments, because the thumb member 1552, and finger members 1554, 1556, 1558, and 1560 are longer, these can be made cut shorter by an attending healthcare worker to better fit the patient. In some embodiments of the invention, the glove 700, comprising slit 740, may be cut-and-sewn or knitted so that glove 700 can fit either a left-hand or a right-hand, i.e., be ambidextrous.

Embodiments of the invention, discussed herein, are directed towards gloves, socks, masks, fingercots, and the like. It is to be further understood that other articles for wound care on other parts of the body are contemplated herein. For example, articles for other parts of the legs, torso, and the like are possible and within embodiments of the invention. Other articles in accordance with embodiments of the invention may be designed and placed over joints, such as the elbow, knee, ankle, hip, shoulder, and the like, which contain all features of embodiments of the invention. Moreover, an article for a joint, for example, a glove extending past the wrist, may be combined with a substantially cylindrical compression sleeve, as could be manufactured by knitting the two components together in a single knitting operation, to form an article that addresses more than one body part. Furthermore, the combination of a glove having a compression sleeve can be made purposely long. Subsequently, the article can be cut shorter by an attending healthcare worker to better fit the patient or to cover only as much of the impacted body part. Embodiments of the invention also include a compression sleeve attached or knitted integrally with an article for an ankle or knee extending to the calf or to the thigh. An article made for an elbow could similarly have a compression sleeve attached that extended long enough for use with the upper arm or forearm or both.

All ranges of numerical values for any dimension recited herein are exemplary, are not to be considered limiting, and include ranges therebetween, and can be inclusive or exclusive of the endpoints. Optional included ranges can be from integer values therebetween, at the order of magnitude recited or the next smaller order of magnitude. For example, if the lower range value is 0.1, optional included endpoints can be 0.2, 0.3, 0.4 . . . 1.1, 1.2, and the like, as well as 1, 2, 3 and the like; if the higher range is 8, optional included endpoints can be 7, 6, and the like, as well as 7.9, 7.8, and the like.

While the foregoing is directed to embodiments of the invention, other embodiments of the invention may be devised without departing from the scope thereof, and the scope thereof is determined by the following claims.

The invention claimed is:

1. A wound care glove, comprising:
    a palm half having a first plurality of finger members and thumb member;
    a backhand half having a second plurality of finger members and thumb member corresponding to the first plurality of finger members and thumb member of the palm half, wherein the at least one of the first plurality of finger members and thumb member and the second plurality of finger members and thumb member are longer, forming
    a plurality of finger flaps for helically wrapping fingers about a lateral axis, the finger flaps having fasteners at distal ends to releasably open and close the finger flaps for viewing a wound;
    wherein the glove comprises a knitted first outer layer comprising a first yarn, the yarn comprising an elastic yarn and silver-containing nylon yarn; and
    a knitted second skin-contacting inner layer comprising a second yarn, the second yarn being a hydrophilic yarn that comprises silver, wherein the second yarn promotes the wicking of moisture to the first outer layer and the transport of silver ions to the wound.

2. The wound care glove of claim 1, wherein the first yarn comprises a hydrophilic yarn.

3. The wound care glove of claim 2, wherein the second layer comprises a nylon yarn.

4. The wound care glove of claim 3, wherein the nylon yarn comprises nylon 6, nylon 6,6 or a Nilit® AQUARIUS yarn.

5. The wound care glove of claim 1, wherein the second yarn further comprises at least one of gold, copper, iodine, or zinc or their alloys, a noble metal-ion, TRIOSYN®, triclosan, 2-propanol, n-halamines, polymeric biguanides, quaternary ammonium compounds, chlorhexidine gluconate, silver-zinc and silver-copper zeolites, or compounds and combinations thereof.

6. The wound care glove of claim 1, further comprising a moisture reservoir fluidly coupled with at least one of the first or second layer.

7. The wound care glove of claim 6, wherein the moisture reservoir further comprises an electrospun polyurethane and bound acrylate.

8. The wound care glove of claim 6, wherein the moisture reservoir comprises SNS NANOSORB® 28, polyacrylates, polyvinyl alcohol, or other hydrogel or hydrophilic particles.

9. The wound care glove of claim 1, further comprising knitted conduits capable of receiving a resilient member.

10. The wound care glove of claim 1, further comprising a dressing, the dressing covering at least one of the first or second layer.

11. A kit, comprising:
    the wound care glove of claim 1, the second yarn comprising a nylon yarn having an antimicrobial agent disposed thereon; and
    an absorbent overarticle for releasably covering the wound care glove, wherein the absorbent overarticle comprises a yarn having cotton fibers, elastomeric fibers and silver-containing nylon fibers.

12. The kit of claim 11, further comprising at least one wound care article, wherein the wound care article is one of an anklet, sock, mask, fingercot, sleeve, compression sleeve, elbow support, or knee support.

13. The kit of claim 11, wherein the wound care article comprises cotton and nylon.

* * * * *